US009080148B2

(12) United States Patent
Isacoff et al.

(10) Patent No.: US 9,080,148 B2
(45) Date of Patent: Jul. 14, 2015

(54) NEURONAL CELLS CULTURED ON MICROPARTICLES AND METHODS OF USING THE NEURONAL CELLS

(75) Inventors: Ehud Y. Isacoff, Berkeley, CA (US); Sophie Pautot, Dresden (DE)

(73) Assignee: The Regents of the University of California, Oakland, CA (US)

( * ) Notice: Subject to any disclaimer, the term of this patent is extended or adjusted under 35 U.S.C. 154(b) by 705 days.

(21) Appl. No.: 12/830,999

(22) Filed: Jul. 6, 2010

(65) Prior Publication Data

US 2011/0014643 A1    Jan. 20, 2011

Related U.S. Application Data

(60) Provisional application No. 61/225,426, filed on Jul. 14, 2009.

(51) Int. Cl.
*C12N 5/079* (2010.01)
*C12N 5/0793* (2010.01)
*C12Q 1/02* (2006.01)
*A61K 35/12* (2015.01)

(52) U.S. Cl.
CPC .............. *C12N 5/0619* (2013.01); *A61K 35/12* (2013.01); *C12N 2501/06* (2013.01); *C12N 2533/12* (2013.01); *C12N 2533/32* (2013.01)

(58) Field of Classification Search
CPC ............. C12N 5/0619; C12N 2533/32; C12N 2501/06; C12N 2533/12; A61K 35/12
USPC ........................................................ 435/403
See application file for complete search history.

(56) References Cited

U.S. PATENT DOCUMENTS

2009/0098183 A1*    4/2009    Detamore et al. ............ 424/423

FOREIGN PATENT DOCUMENTS

WO    WO 2005037985 A2 *    4/2005    .............. C12M 3/00

OTHER PUBLICATIONS

Pautot et al. Colloid-guided assembly of oriented 3D neuronal networks. Nature Methods. vol. 5 No. 8 Aug. 2008 p. 735-740.*
Morrison et al. Basic fibroblast growth factor supports the survival of cerebral cortical neurons in primary culture. Proc. Nati. Acad. Sci. USA vol. 83, pp. 7537-7541, Oct. 1986.*
Delgado-Martinez et al. Differential Abilities of SNAP-25 Homologs to Support Neuronal Function. The Journal of Neuroscience, Aug. 29, 2007 • 27(35):9380-9391.*
Beaulieu, C. & Colonnier, M. The number of neurons in the different laminae of the binocular and monocular regions of area 17 in the cat, Canada *J. Comp. Neurol.* 217, 337-44 (1983).
Changeux, J. P. & Dehaene, S. Neuronal models of cognitive functions. *Cognition* 33, 63-109 (1989).
Chiappalone, M. et al. Networks of neurons coupled to microelectrode arrays: a neuronal sensory system for pharmacological applications. *Biosens. Bioelectron.* 18, 627-34 (2003).
Golomb, D. & Hansel, D. The number of synaptic inputs and the synchrony of large, sparse neuronal networks. *Neural Comput.* 12, 1095-139 (2000).
Gorostiza, P. et al. Mechanisms of photoswitch conjugation and light activation of an ionotropic glutamate receptor. *Proc. Natl. Acad. Sci. USA* 104, 10865-70 (2007).
Hofmann, F. & Bading, H. Long term recordings with microelectrode arrays: studies of transcription-dependent neuronal plasticity and axonal regeneration. *J. Physiol. Paris.* 99, 125-32 (2006).
Huang, Y. C. & Huang, Y. Y. Biomaterials and strategies for nerve regeneration. *Artif. Organs* 30, 514-22 (2006).
Ikeda, S. R. Expression of G-protein signaling components in adult mammalian neurons by microinjection. *Methods Mol. Biol.* 259, 167-81 (2004).
Jun, S. B. et al. Low-density neuronal networks cultured using patterned poly-llysine on microelectrode arrays. *J. Neurosci. Methods.* 160, 317-26 (2007).
Letourneau, P. C. Cell-to-substratum adhesion and guidance of axonal elongation. *Dev. Biol.* 44, 92-101 (1975).
Letourneau, P. C. Possible roles for cell-to-substratum adhesion in neuronal morphogenesis. *Dev. Biol.* 44, 77-91 (1975).
Lo, Y. J. & Poo, M. M. Heterosynaptic suppression of developing neuromuscular synapses in culture. *J. Neurosci.* 14, 4684-93 (1994).
Miyoshi, H. et al. Development of a self-inactivating lentivirus vector. *J. Virol.* 72, 8150-7 (1998).
Morin, F. et al. Constraining the connectivity of neuronal networks cultured on microelectrode arrays with microfluidic techniques: a step towards neuron-based functional chips. *Biosens. Bioelectron.* 21, 1093-100 (2006).
Pusey, P. N. & Vanmegen, W. Phase-Behavior of Concentrated Suspensions of Nearly Hard Colloidal Spheres. *Nature* 320, 340-342 (1986).
Schmidt, C. E. & Leach, J. B. Neural tissue engineering: strategies for repair and regeneration. *Annu. Rev. Biomed. Eng.* 5, 293-347 (2003).

(Continued)

*Primary Examiner* — Taeyoon Kim
(74) *Attorney, Agent, or Firm* — Edward J. Baba; Shweta Chandra; Bozicevic, Field & Francis LLP

(57) ABSTRACT

The present invention provides methods for culturing neuronal cells for transplantation into a subject. The methods include culturing neuronal cells with microparticles to provide a microparticle and neuronal cell culture composition, wherein the microparticles are coated with a compound that provides for attachment of neuronal cells. The present invention also provides methods of screening the cultured neuronal cells as well as kits and systems for the method of screening.

14 Claims, 8 Drawing Sheets

(56) References Cited

OTHER PUBLICATIONS

Shany, B. et al. Growth of primary hippocampal neuronal tissue on an aragonite crystalline biomatrix. *Tissue Engineering* 11, 585-596 (2005).
Shepherd, G. M. Microcircuits in the nervous system. *Sci. Am.* 238, 93-103 (1978).
Song, H. J. et al. cAMP-induced switching in turning direction of nerve growth cones. *Nature* 388, 275-9 (1997).
Szobota, S. et al. Remote control of neuronal activity with a light-gated glutamate receptor. *Neuron* 54, 535-45 (2007).
Van Blaaderen, A. et al. Template-directed colloidal crystallization. *Nature* 385, 321-324 (1997).
Volgraf, M. et al. Allosteric control of an ionotropic glutamate receptor with an optical switch. *Nat. Chem. Biol.* 2, 47-52 (2006).
Wickersham, I. R. et al. Monosynaptic restriction of transsynaptic tracing from single, genetically targeted neurons. *Neuron* 53, 639-47 (2007).
Wickersham, I. R. et al. Retrograde neuronal tracing with a deletion-mutant rabies virus. *Nat. Methods* 4, 47-9 (2007).
Wyart, C. et al. Constrained synaptic connectivity in functional mammalian neuronal networks grown on patterned surfaces. *J. Neurosci. Methods.* 117, 123-31 (2002).
Xiang, G. et al. Microelectrode array-based system for neuropharmacological applications with cortical neurons cultured in vitro. *Biosens. Bioelectron.* 22, 2478-84 (2007).

\* cited by examiner

NEURONAL CELLS CULTURED ON MICROPARTICLES AND METHODS OF USING THE NEURONAL CELLS

CROSS-REFERENCE

This application claims the benefit of U.S. Provisional Patent Application No. 61/225,426, filed Jul. 14, 2009, which application is incorporated herein by reference in its entirety.

GOVERNMENT RIGHTS

This invention was made with government support under federal grant nos. PN2 EY1018241 awarded by the National Institutes of Health. The United States Government has certain rights in this invention.

BACKGROUND OF THE INVENTION

A central challenge in Neuroscience is to understand how complex three-dimensional networks of neuronal cells form synapses and generate neuronal activity. Traditional neuronal cell culture requirements and electrophysiological techniques have limited in vitro studies of neuronal cells to the examination of relatively few cells interacting in only two dimensions. In order to study the principles of neuronal network formation in native neuronal tissue, in vitro methods must be developed to allow for high cell density and connectivity, while simultaneously enabling controlled gene expression and non-invasive techniques for examining and stimulating individual cells. Currently available biomaterials have failed to support neuronal cell branching in three dimensions at an appropriate scale.

Neuronal degeneration is at the origin of many neurological disorders. Since the mammalian central nervous system has a limited capacity for self-repair, tissue replacement has been explored as a treatment option for many neurological disorders. However, tissue replacement techniques have only found limited success because neuronal cells are highly differentiated and have delicate processes. Transplantation of neuronal cells typically results in a loss of the differentiated phenotype and/or damage to the neuronal cell processes. Transplantation of non-differentiated cells, such as stem cells, has had some limited success, but only a small fraction of the transplanted cells differentiate into the desired neuronal cell phenotype, and most fail to integrate into the surrounding native neuronal tissue.

The present invention addresses these needs.

SUMMARY OF THE INVENTION

The present invention provides methods for culturing neuronal cells for transplantation into a subject. The methods include culturing neuronal cells with microparticles to provide a microparticle and neuronal cell culture composition, wherein the microparticles are coated with a compound that provides for attachment of neuronal cells. The present invention also provides methods of screening the cultured neuronal cells as well as kits and systems for use in the same.

These and other objects, advantages, and features of the invention will become apparent to those persons skilled in the art upon reading the details of the neuronal cells cultured on microparticles as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1, Panel a and FIG. 1, Panel b show E18 hippocampal neurons that were cultured in different media and imaged at DIV 3. Cells were fixed and stained with a neuron specific alpha-tubulin antibody (green), and a glia specific GFAP antibody (red). In normal media (FIG. 1, Panel a) neurons grow extensive processes and some of these processes are entangled with glia (arrow). In media containing the mitotic inhibitor araC (FIG. 1, Panel b), neuronal processes are shorter. Following 14 days in media containing araC and conditioned with feeder glial cells, neuronal processes (seen from alpha-tubulin antibody, green, and synapses seen from synapsin antibody, red) have grown extensively. The example shown in FIG. 1, Panel c is from a bead with a single neuron, which formed synapses onto itself. The arrow indicates the neuronal cell body. FIG. 1, Panels d-i show the effect of support size. Neurons were seeded at the same surface density on 45 µm (FIG. 1, Panels d-f) and 125 µm (FIG. 1, Panels g-i) PLL-coated beads. At DIV 4, both cultures were fixed and stained with a neuron specific Tuj-1 antibody (green) and with an axon specific smi-312 antibody (red). Neurons were polarized in both preparations independently of bead radius of curvature. The number of neurons per bead was proportional to the bead surface area; a 45 µm bead carried, on average, one tenth of the cells carried by the 125 µm beads. Scale bars=50 µm. FIG. 1, Panels 1-j show interfacing neurons. Neurons expressing the presynaptic adhesion protein neurexin-RFP (red) were cultured on poly-L-lysine coated glass. Neurons expressing cytosolic eGFP (green) were cultured on poly-L-lysine coated beads. After a week in culture, beads were added onto the 2D neuron culture. Scale bar=10 µm. FIG. 1, Panel j is a schematic representation of the image plane. FIG. 1, Panel k is a TIRM image of the plane of contact. Arrows indicate points of contact between cells. FIG. 1, Panel l shows neurons at DIV 14 in conditioned media with araC. Neuronal processes stained with alpha-tubulin antibody (green); pre-synaptic terminals stained with synapsin antibody (red). Processes can be seen crossing between beads to make synaptic contact on neighboring neurons. Beads are 125 µm in diameter.

FIG. 2, Panel b shows two sets of neurons cultured on beads. The neuronal cells were infected on DIV 2 with lenti virus driving the expression of GFP, in one case, and monomeric TandemDimerTomato, in the other. The two bead populations were mixed together on DIV 4 and spontaneously formed a 2D ordered array of green and red expressing neurons.

FIG. 3, Panel b shows a three-week-old culture of a three-dimensional neuronal network assembly, fixed and stained with the neuron-specific anti-alpha tubulin antibody (green) and the glial-specific anti-GFAP antibody (red). Five layers, a (450×450×388 µm) volume of the assembly, were imaged by confocal microscopy. The images extracted from the z-stack for the green and red channels (left) are shown with schematic representations of the corresponding layer position (right). FIG. 3, Panel c shows expanded views of regions (grey rectangles) from top and bottom layers in FIG. 3, Panel b, wherein the details of the cells and their processes wrapped around the beads can be seen. FIG. 3, Panel d shows the scaling of the number of beads per unit volume with bead size. Each point is labeled with the corresponding bead radius. FIG. 3, Panel e shows the relationship between the volume density of cells and cell seeding conditions. Each point is labeled with the corresponding number of cells per bead. The most effective way to increase cell density, while maintaining a small number of cells per bead, is to keep bead size to a minimum.

FIG. 4, Panel a shows neurons that were cultured in 2D on a cover slip (layer 1) for about one week (DIV 5-7) before cAMP-coated 45 µm beads, which contained no neurons of their own, were layered on top of them (schematic on right). Three days later, the culture was fixed and stained with smi-312, an axon specific antibody (red). Confocal microscopy z series starting 5 µm above the 2D culture and ending at the top of the bead was projected in 3D and shown here (left). Axons from neurons on the cover slip grew onto the surface of the overlying cAMP-coated beads (arrow marks point where an axon leaves the cover slip for the bead surface; asterisk marks the end of the growing axon). In FIG. 4, Panels b-j, axons from neurons on the cover slip (layer 1, FIG. 4, Panels b-d) represent most of the processes in the cAMP-coated beads (layer 2) 2 days after the bead layer is formed (FIG. 4, Panels e-g) and these grow extensively over the next 5 days (FIG. 4, Panels h-j). Cells were fixed and stained for neuronal (Tuj-1, red) and axonal (smi-312, blue) markers 2 days (FIG. 4, Panels b-g) or 7 days (FIG. 4, Panels h-i) after addition of the cAMP bead layer. FIG. 4, Panels k-r show that GFP-expressing neurons in a layer of beads (added after a delay on top of layer 2) extend dendrites down through the cAMP bead layer. FIG. 4, Panel k is a schematic of the arrangement of two layers of beads on a cover slip. FIG. 4, Panel l is a 3D reconstruction of axons (blue) from neurons on the cover slip (layer 1) growing up into the intermediate layer of cAMP beads (layer 2) and there encountering dendrites descending from the bead layer (layer 3) of GFP-expressing cells (green). Layer 3 was added 2 days after layer 2. FIG. 4, Panels m-r show that the dendrites of the GFP cells in layer 3 reach down as far as layer 1. Optical sections shown only in layer 1, labeled for all processes (Tuj-1, red), axons (smi-312, blue) and GFP from upper layer 3 (green). Scale bars=100 µm.

In FIG. 5, Panel b, LiGluR6 is shown in the cell membrane of the cover slip neurons in both resting state, where the MAG photoswitch is in the trans state and points its glutamate away from the binding pocket, and following illumination with violet light (390 nm), which photoswitches the MAG into the cis state, allowing the glutamate to bind and open the channel, leading to influx of Ca++ to excite the neuron. FIG. 5, Panels c-d show photoswitching of neuronal activity as detected by rises in Ca++ using the rhod-2 indicator. Illumination with 390 nm light excites the LiGluR6 neurons on the cover slip (lower image and rhod-2 fluorescence traces), and illumination at 542 nm turns the excitation off. Traces correspond to Rhod-2 fluorescence change ($\Delta F/F$) as illumination changes. The violet bar above the traces on the right indicates the timing of illumination at 390 nm Optical stimulation also excites GFP-expressing layer-3 neurons (upper image and traces), which do not express LiGluR, indicating that they receive excitatory inputs from cells in layer 1. Responses for four cells on cover slip and four cells on a bead in layer 3 are color coded, as indicated, and superimposed. Responses in the postsynaptic layer-3 cells were generally smaller. In some cases, the responses of the layer-3 neurons to optical stimulation of the layer-1 neurons were relatively uniform in amplitude (FIG. 5, Panel c), while in other cases, the response amplitudes in layer 3 differed considerably from cell to cell, even on the same bead (FIG. 5, Panel d).

FIG. 6, Panel a is a bright field image of a brain slice in the injected region. FIG. 6, Panel b is a montage of contiguous frames showing the extent of the transplanted neuron (P0 DIV4) implantation in the area marked by the rectangle a week post injected.

FIG. 7, Panel a is a bright field image of the brain slice area imaged, and binary schematic of the hippocampus to highlight neuron locations. FIG. 7, Panels b-c show mature GFP-neurons transplanted using 45 µm bead carriers. FIG. 7, Panel b is a cross-section of a bead carrying two GFP-neurons sending processes into the hippocampus. FIG. 7, Panel c shows GFP-neuron development in the CA3 region. FIG. 7, Panel d shows mature GFP-neurons dissociated from bead support prior to injection.

FIG. 8, Panel d shows an overlay of both channels. Scale bar=100 µm. LiGluR6 cell was stimulated by short exposure to 390 nm light for short period of time and we record the calcium response of the surrounding neurons. FIG. 8, Panel a1-a5 show calcium variation of an individual cell (single pixel) after binning (3×3) and subtraction of the fluorescence background. Response was color-coded using a rainbow scale. Corresponding fluorescence intensity changes during UV stimulation are shown in FIG. 8, Panel e. All neurons in the slice responded to the stimulation indicating that the transplanted cell has made functional connections with the surrounding neurons. For 6 neurons distributed above (FIG. 8, Panel a1-a5, labeled a, b, c) and below (FIG. 8, Panel a1-a5, labeled 1, 2, 3) the transplanted cell we calculated $\Delta F/F$ for seven UV stimulations (FIG. 8, Panel f). $\Delta F/F$ of the LiGluR neuron remains around 30% (+/−2.5%). Neurons a, b, and c have, on average, higher $\Delta F/F$ than the stimulated neurons with significant variations from one exposure to the next, while neurons 1, 2, and 3 have, on average, a smaller $\Delta F/F$.

Figure 1:
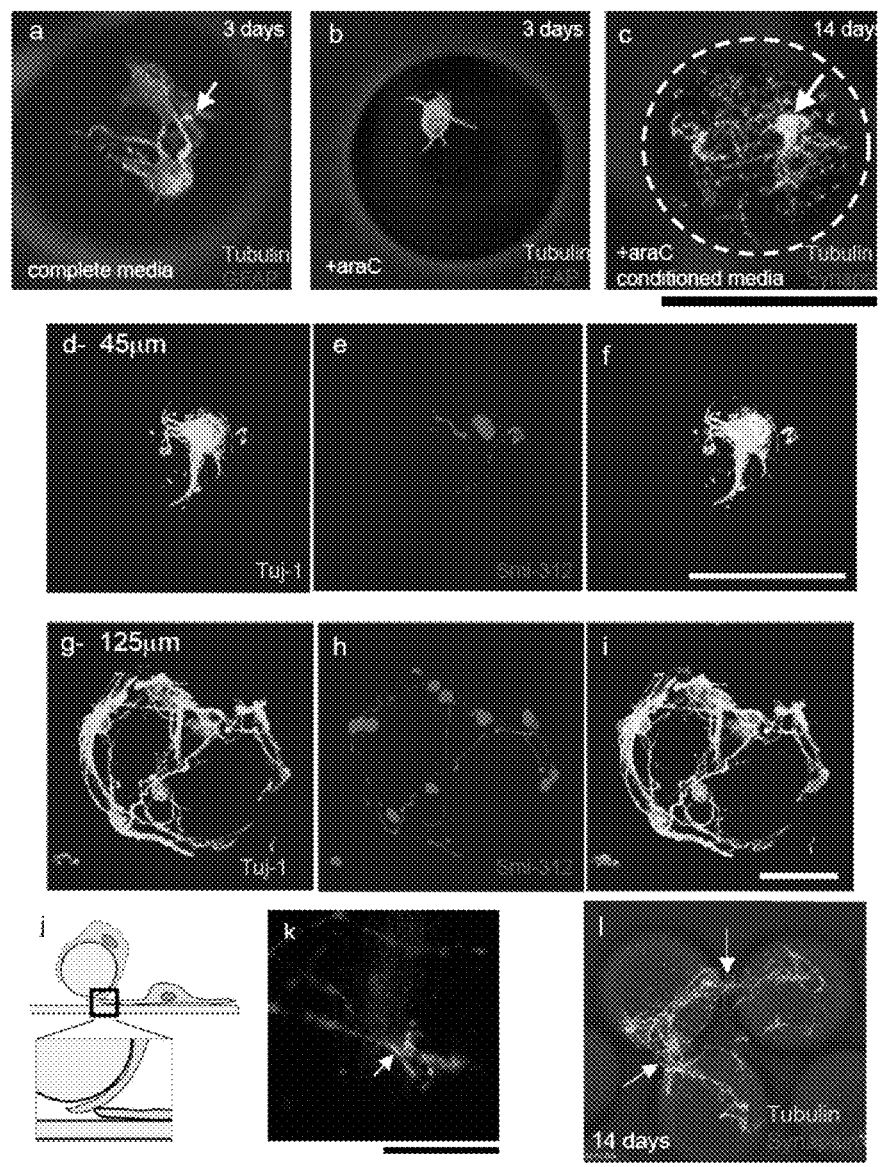
FIG. 1 shows development and manipulation of neurons supported on silica beads. Confocal microscopy z series are projected on the xy scanning plane. The bright field image is overlaid to indicate the location of the bead. Scale bar=100 µm.

Before the present invention is described, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a neuronal cell" includes a plurality of such neuronal cells and reference to "a microparticle" includes reference to one or more microparticles and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides a method for culturing neuronal cells on microparticles that are capable of spontaneously forming into ordered, two-dimensional layers. The microparticles can be coated with agents that facilitate adhesion of neuronal cells. Neuronal cells can then be attached to the microparticles, providing a portable growth surface. The microparticles with attached neuronal cells can be placed in a tissue culture dish, where they spontaneously form an ordered, two-dimensional layer, due to the properties of the microparticles. The two-dimensional layer of microparticles with attached neuronal cells can be maintained in culture, and the neuronal cells can be assayed for neuronal activity. Culturing neuronal cells on microparticles allows the cells to be moved and transfected without damaging the delicate axons and dendrites that are characteristic of differentiated neuronal cells.

Multiple layers of microparticles with or without attached cells can be built up to form three-dimensional structures that simulate the cell density and cell-cell interactions that are present in native neuronal tissues. Further, the microparticles can be coated with agents of interest that can modulate neuronal cell activity. Such agents may stimulate the formation of functional connections between neighboring neuronal cells in the three-dimensional structure, or may inhibit such interaction. The structures therefore provide a platform that can be used to screen agents of interest for the ability to modulate neuronal cell activity and the formation of functional neuronal cell networks. Such agents may be useful in treating various neurological disorders.

The portability of the microparticle growth surface also allows the neuronal cells to be transplanted, either into other cultures, or directly into subjects, such as animals and humans. The microparticles can be moved without disrupting the adhesion of the neuronal cells or damaging their delicate axons and dendrites. When these delicate structures are intact after transplantation, the neuronal cells are more capable of integrating into the recipient's neuronal tissue and forming functional connections with the subject's existing neuronal cells.

In addition, the microparticles provide a growth surface that enables neuronal cells to interact in ways that closely mimic the environment found in native neuronal tissues. When neuronal cells are cultured on microparticles, the neuronal cells can be moved, transfected, and cultured without disrupting their adhesion and without damaging their delicate processes. Moreover, microparticles can spontaneously assemble into uniform two-dimensional layers that provide an organized structure on which neuronal cells can grow and communicate with one another. These uniform layers can be stacked to form three-dimensional structures, providing an environment that more closely simulates the cell densities and cell-cell interactions of native neuronal tissues. Neuronal cells grown in such three-dimensional structures therefore provide an opportunity to study the principles that govern formation of neuronal cell networks in vivo. Further, neuronal cells grown in such three-dimensional structures can be transplanted into animals because the microparticles allow for manipulation of the cells without damaging their delicate processes.

Methods and Compositions

The present invention provides methods for culturing neuronal cells for transplantation into a subject. The invention involves contacting a first population of microparticles with neuronal cells to provide a microparticle and neuronal cell composition. The population of microparticles is coated with a compound that provides for attachment of neuronal cells. The method also involves depositing the microparticle and neuronal cell composition on a solid substrate. This depositing forms a first two-dimensional layer of the microparticle and neuronal cell composition.

The present invention also provides methods for culturing neuronal cells for transplantation into a subject where the first population of microparticles with neuronal cells to provide a microparticle and neuronal cell composition, wherein the first population of microparticles is coated with a compound that provides for attachment of neuronal cells, and depositing the microparticle and neuronal cell composition on a solid substrate, wherein the depositing forms a first two-dimensional layer of the microparticle and neuronal cell composition, and depositing a second population of microparticles, wherein the depositing forms a second two-dimensional layer of the microparticles, wherein the second two-dimensional layer is disposed on the surface of the first two-dimensional layer, or is disposed in between the first two-dimensional layer and the solid surface.

The present invention also provides methods for culturing neuronal cells for transplantation into a subject by contacting a first population of microparticles with neuronal cells to provide a first microparticle and neuronal cell composition, wherein the first population of microparticles is coated with a compound that provides for attachment of neuronal cells, and depositing the first microparticle and neuronal cell composition on a solid substrate, wherein the depositing forms a first two-dimensional layer of the first microparticle and neuronal cell composition, and depositing a second population of microparticles on the surface of the first two-dimensional layer, wherein the depositing forms a second two-dimensional layer of the microparticles, and contacting a third population of microparticles with neuronal cells to provide a second microparticle and neuronal cell composition, wherein the third population of microparticles is coated with a compound that provides for attachment of neuronal cells, and depositing the second microparticle and neuronal cell composition on the surface of the second two-dimensional layer of microparticles, wherein the depositing forms a third two-dimensional layer of the second microparticle and neuronal cell composition.

In some embodiments, the neuronal cells are assayed for neuronal activity. In certain embodiments, the assaying for neuronal activity involves staining the neuronal cells with an agent that binds specifically to a neuronal cell process. In some embodiments, the neuronal cell process is a dendrite or an axon. In certain embodiments, the neuronal cells are transfected with a gene of interest encoding a detectable molecule and the neuronal cells are assayed for neuronal activity by detecting the detectable molecule. In certain embodiments, the neuronal activity comprises growth of a neuronal cell process. In some embodiments, the neuronal cell process is a dendrite or an axon. In certain embodiments, the detectable molecule is a fluorescent protein optionally under the control of a conditional promoter, such as a synapsin promoter. In some embodiments, the fluorescent protein is Green Fluorescent Protein or Tandem-Dimer-Tomato. In certain embodiments, the detectable molecule is a light-gated glutamate receptor. In some embodiments, the microparticles are contacted with a candidate agent. In certain embodiments, the neuronal cells are cultured in medium that contains a mitotic inhibitor. In some embodiments, the mitotic inhibitor is araC. In certain embodiments, the microparticles are silica beads, latex beads, agarose beads, collagen beads, polyacrylamide beads, poly-L-lysine (PLL) coated beads, or poly(lactic-co-glycolic acid) (PLGA) beads. In some embodiments, the compound that provides for attachment of neuronal cells is poly-L-lysine.

The present invention also provides methods for identifying a candidate agent that modulates neuronal cell activity, wherein a neuronal cell culture is contacted with a candidate agent, wherein the neuronal cell culture comprises a first two-dimensional layer of microparticles and neuronal cells, wherein the microparticles are coated with a compound that provides for attachment of neuronal cells, and assaying the neuronal cell culture for neuronal activity in the presence of the candidate agent, wherein the assaying for neuronal activity involves comparing the neuronal activity in the presence of the candidate agent to neuronal activity in the absence of the candidate agent, wherein a change in the neuronal activity indicates that the candidate agent modulates neuronal cell activity.

In some embodiments, the assaying for neuronal activity comprises contacting the neuronal cells with an agent that binds specifically to a neuronal cell process. In certain embodiments, the neuronal cell process is a dendrite or an axon. In some embodiments, the neuronal cells are transfected with a gene of interest encoding a detectable molecule, and the neuronal cells are assayed for neuronal activity by detecting the detectable molecule. In certain embodiments, the neuronal activity comprises growth of a neuronal cell process. In some embodiments, the neuronal cell process is a dendrite or an axon.

In certain embodiments, the detectable molecule is a fluorescent protein optionally under the control of a conditional promoter, such as a synapsin promoter. In some embodiments, the fluorescent protein is Green Fluorescent Protein or Tandem-Dimer-Tomato. In certain embodiments, the detectable molecule is a light-gated glutamate receptor. In some embodiments, the microparticles are contacted with a candidate agent. In certain embodiments, the neuronal cells are cultured in medium that contains a mitotic inhibitor. In some embodiments, the mitotic inhibitor is araC. In certain embodiments, the microparticles are silica beads, latex beads, agarose beads, collagen beads, polyacrylamide beads, poly-L-lysine (PLL) coated beads, or poly(lactic-co-glycolic acid) (PLGA) beads. In some embodiments, the compound that provides for attachment of neuronal cells is poly-L-lysine. In some embodiments, the culture of neuronal cells additionally comprises a second two-dimensional layer of microparticles and neuronal cells.

The present invention also provides methods for transplanting neuronal cells into a subject by culturing neuronal cells for transplantation, wherein the culture of neuronal cells comprises a first two-dimensional layer of microparticles and neuronal cells, wherein the microparticles are coated with a compound that provides for attachment of neuronal cells, and transplanting the neuronal cell culture into a subject. In some embodiments, the subject is a mammal. In certain embodiments, the mammal is a non-human animal.

The present invention also provides a non-human animal comprising a transplanted neuronal cell culture, wherein the neuronal cell culture comprises a first two-dimensional layer of microparticles and neuronal cells, wherein the transplanted neuronal cells induce neuronal activity in host neuronal cells of the non-human animal. In some embodiments, the neuronal cell culture further comprises microparticles that are coated with a compound that provides for attachment of neuronal cells. In certain embodiments, the culture of neuronal cells additionally comprises a second two-dimensional layer of microparticles and neuronal cells.

The present invention also provides a non-human animal comprising a transplanted culture of neuronal cells, wherein the transplanted culture of neuronal cells comprises a first two-dimensional layer of microparticles and neuronal cells, wherein the microparticles are coated with a compound that provides for attachment of neuronal cells, and wherein the transplanted culture of neuronal cells induces neuronal activity in host neuronal cells of the non-human animal. In some embodiments, the transplanted neuronal cells are allogenic to the non-human animal.

In some embodiments, the transplanted neuronal cells are xenogenic to the non-human animal. In some embodiments, the transplanted neuronal cells are human cells. In some embodiments, the culture of neuronal cells additionally comprises a second two-dimensional layer of microparticles and neuronal cells.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials were used in the examples below.

Neuron culture on prepared silica beads:

Borosilicate Glass Spheres (MO-SCI Specialty Products, Rolla, Mo.) were sterilized in an ethanol solution overnight, and dried under vacuum. Then the beads were incubated in a borate buffer solution for one hour, before being left in PLL solution overnight. Hippocampi were removed from embryonic day 18 (E18) rats and treated with trypsin for 20 min at 37° C., followed by washing and trituration. Dissociated cells were plated at 75,000 cells/cm$^2$ on poly-lysine-coated glass beads and cultured in neurobasal medium supplemented with 2 mM Glutamax, 2% FBS, and 2% B-27. Cells were transfected with Lipofectamine 2000 (Invitrogen) or they were infected with lenti virus after 5-15 days after dissociation and analyzed 2-14 days after infection.

Immuno-Staining:

Anti-alphaTubulin, anti-GFAP, and anti-Synapsin-I antibodies were purchased from Chemicon International (Temecula, Calif.). Anti-smi-312 and anti-Tuj-1 were obtained from Covance (Berkeley, Calif.). Anti-GFP and Nissl-red were purchased from Invitrogen.

Animal Surgeries and Histology:

DIV 5 neurons cultured on 45 µm beads were stereotactically injected into the right hippocampus of the brain (anteroposterior [AP], −3.5; mediolateral [ML], 3.0; dorsoventral [DV], −3.9 from skull) of adult female Fischer 344 rats (150 g, 6 weeks old). The animals were deeply anesthetized with a mixture of ketamine (90 mg/kg) and xylazine (10 mg/kg) before injection, and 0.5 µl of the bead suspension (~34 beads on average) was injected with a Hamilton syringe. One week post-injection, the animals were transcardially perfused with 4% paraformaldehyde (PFA) in phosphate buffered saline (PBS), and the brains were excised to assess the implantation of the injected neurons through quantification of GFP expression (n=6 animals). The retrieved brains were post-fixed by immersion in 4% PFA overnight at 4° C. and subsequently stored in 30% sucrose for cryoprotection before sectioning. Coronal sections (thickness, 100 µm) were cut with a VIBRATOMET™.

GFP expression was amplified with primary rabbit anti-GFP. Corresponding secondary antibodies (labeled with Alexa Fluor 488) were used for detection. For nuclear staining, sections were stained with Nissl-red. The sections containing regions exhibiting GFP expression were collected and imaged on an inverted confocal microscope (Zeiss LSM 510 Axiovert 200) using 20× air objective and 40× oil objective (1.3 N.A.).

Animal protocols were approved by the University of California, Berkeley (UCB) Animal Care and Use Committee and conducted in accordance with National Institutes of Health (NIH, Bethesda, Md.) guidelines.

Brain Slice Preparation for Functional Activity:

Rats were anaesthetized by halothane and killed by decapitation one week after the intracranial injection, in accordance with institutional guidelines. Horizontal midbrain slices (250-µm thick) were cut using a VIBRATOME™ (Vibratome Company). Slices were prepared at 4-6° C. in a solution containing 110 mM choline chloride, 2.5 mM KCl, 1.25 mM NaH$_2$PO$_4$, 0.5 mM CaCl$_2$, 7 mM MgSO$_4$, 26 mM NaHCO$_3$, 25 mM glucose, 11.6 mM sodium ascorbate and 3.1 mM sodium pyruvate. The slices were incubated in artificial cerebrospinal fluid (ACSF) containing 125 mM NaCl, 3 mM KCl, 2 mM CaCl$_2$, 1 mM MgCl$_2$, 1.25 mM NaH$_2$PO$_4$, 26 mM NaHCO$_3$ and 10 mM glucose. The solutions were saturated with 95% O$_2$ and 5% CO$_2$.

MAG Labeling and Illumination Protocol:

Conjugation of MAG-1 to LiGluR6 (L439C) in hippocampal neurons for optical switching experiments was based on the method described earlier. {Szobota, 2007#90} The compound was diluted to 25 µM in ACSF solution, and preactivated by UV light (365 nm) for 1 min to enhance conjugation by affinity labeling. {Gorostiza, 2007#94} (Gorostiza et al., 2007). Cells were incubated in the dark in an appropriate volume of the labeling solution for 15 min at 37° C. Subsequently, cells were loaded for 10-15 min with Rhod-2 (Invitrogen) at 5 µm in 20% pluronic acid and then washed three times with the ACSF solution. After a 15 min recovery period, the cells were examined to confirm neuronal activity. The solutions were saturated with 95% O$_2$ and 5% CO$_2$.

The preparation was imaged on an inverted confocal microscope (Zeiss LSM 510 Axiovert 200) using a 40× oil objective (1.3 N.A.). Neurons were illuminated with 390 nm light (frequency doubled 780 nm) to activate LiGluR6, and with 543 nm light, used both to image Rhod-2 and to deactivate LiGluR6.

Imaging:

Confocal microscopy z series images were acquired on a Zeiss LSM510 confocal microscope with 63× dipping objective (0.9 N.A.), and a Zeiss LSM 510 Axiovert 200 using a 20× air objective and 40× oil objective (1.3 N.A.). Laser power, photomultiplier gain, and filter sets were selected to minimize bleaching and bleed-through between channels (In nm, Alexa488 and GFP: ex 488, em 500-550; Cy3: ex 543, em 565-615; Alexa 647: ex 633, em 650-700).

Example 1

Isolation and Culture of Mammalian Brain Neurons

Rat hippocampal neurons were selected as model mammalian brain neurons. Following dissection at a late embryonic stage (E18), or early postnatal stage (P4), the neurons were dissociated and cultured on beads coated with poly-L-lysine (PLL) to enhance cell adhesion and to support maturation. (13, 14) The neurons were grown on the beads using standard techniques developed for conventional 2D cultures (Pautot et al., 2008). At day 3 in vitro (DIV 3), beads were mainly populated by neurons, and process branching was comparable to that of 2D cultures (FIG. 1, Panel a). However, a small number of supporting glial cells, which contribute to neuronal development by stimulating neuron growth and maturation, were also present. The glia continued to divide over the 7-10 days of neuronal maturation, competing with the neurons for the bead surface and ultimately interfering with neuron adhesion. Thus, for long-term growth it was desirable to keep the number of glia to a minimum. To arrest glial division, the mitotic inhibitor araC was added to the culture media. Under these conditions, neuron outgrowth and branching was slowed and neuron growth was eventually compromised (FIG. 1, Panel b). To restore the glial growth factors, araC was combined with conditioned media from glial feeder cell cultures. This resulted in a robust growth of neurons on the beads over a period of more than 3 weeks, even when the beads only carried single neurons (FIG. 1, Panel c).

Example 2

Modular Assembly of 3D Networks Using Silica Beads

Silica beads larger than 45 µm in diameter were used to provide a growth surface large enough for neuronal cell bodies and their processes. The bead surface was coated with poly-L-lysine (PLL) to enhance cell adhesion and to support neuronal maturation (25, 26). Rat hippocampal neurons were harvested at a late embryonic stage (E18) and cultured on PLL-coated beads following dissection and dissociation. The beads provided a unique type of surface in that they contained between one and a few neurons, and could be easily moved without disrupting neuronal adhesion or damaging the delicate processes. Neurons growing on the beads were transfected by conventional means or using viruses. Following transfection, the neurons on the beads were transferred to other culture dishes. The neuron-coated beads were placed onto conventional 2D neuronal cultures growing on cover slips, and were positioned so that the neurons on the beads came into contact with select cells on the 2D neuronal cover slip cultures. The beads were also laid down on surfaces in groups with a regular geometry. Monodispersed beads (20, 21) assembled spontaneously into 2D ordered arrays (FIG. 2, Panel a) that were layered to form 3D assemblies with controlled neuron packing.

Figure 2:
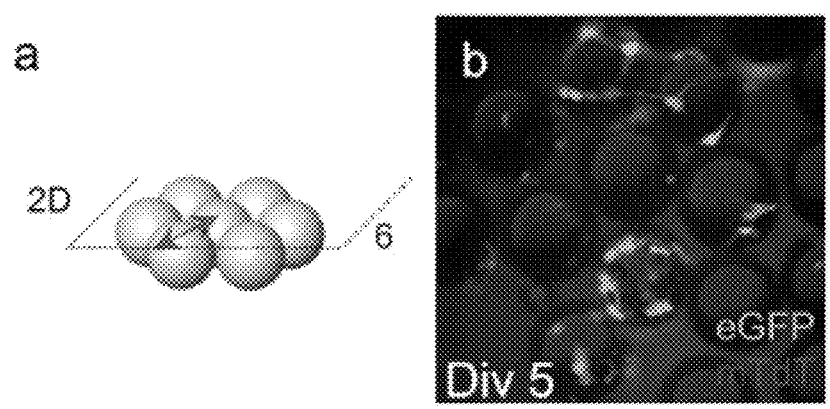
FIG. 2, Panel a is a schematic representation of spontaneous 2D bead assembly.

To illustrate the assembly principle, after two days in vitro (DIV 2), one bead culture was transfected to express Green Fluorescent Protein (GFP) while another was transfected to express Tandem-Dimer-Tomato (TdT). Once the neurons reached maturity on their respective beads, the beads were moved to small wells with a coarse pipette, without removing the cells from their supporting surfaces. The beads settled under gravitational force and spontaneously assembled into 2D hexagonal arrays at the bottom of the wells (FIG. 2, Panel b). Once the first layer was fully packed, additional beads formed a second ordered layer, which had the same hexagonal symmetry (FIG. 2, Panel a). Successive applications of beads constructed a packed 3D assembly with a controlled number of layers.

Figure 3:
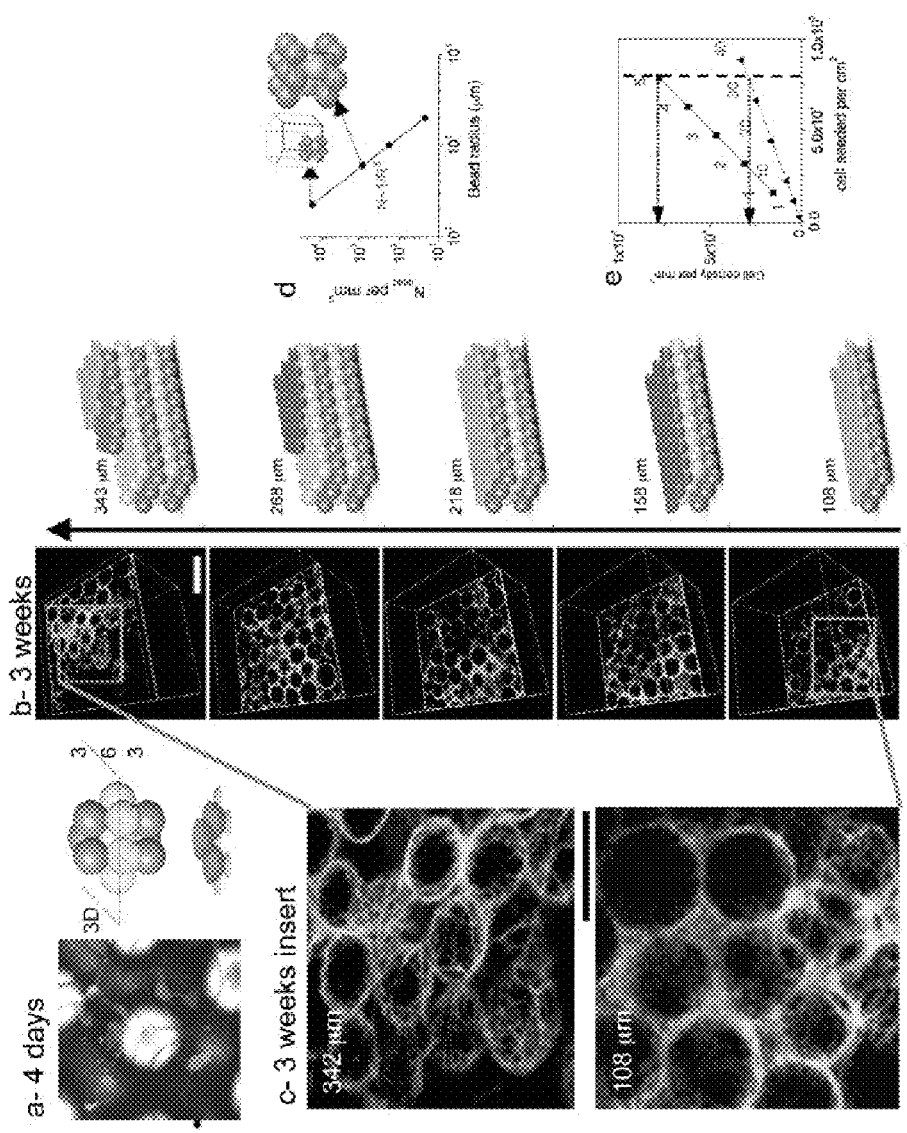
FIG. 3, Panel a shows a two-layer assembly of beads carrying GFP-expressing neurons imaged live by confocal microscopy at DIV 4. Schematic representations (right) show the two layers (top), and a 20 µn deep sub-section of the assembly (bottom) that corresponds to the image (left). The image is an XY projection of a 20 µm (10 frames) confocal z series overlaid with the corresponding bright field image. Scale bar=125 µm.

Over the course of three weeks in culture, following spontaneous assembly of the 3D hexagonal bead arrays, neuronal processes grew between the beads to form highly inter-connected millimeter-sized networks (FIG. 3, Panel b). The assemblies were characterized by acquiring confocal microscopy images of 450 µm×450 µm×388 µm subsections. Frames extracted from the representative z series, together with a corresponding schematic to indicate their position within the assembly, are shown in FIG. 3, Panel b. Neuronal processes, as well as some glial cells, were observed crossing from one bead to the next (FIG. 3, Panel b). The beads were woven together by the crossing processes and formed stable structures (FIG. 3, Panel c). This eliminated the need for exogenous cross-linking agents to hold the arrays together during solution exchange. The void spaces between the beads enabled the necessary media exchange to maintain healthy growing conditions in these dense cultures. The number of cells per bead, as well as the number of neuronal processes, were similar in all layers of the array (FIG. 3, Panel b), indicating that cell health was not affected by location within the assembly.

Example 3

Controlling the Number of Neurons Per Bead

E18 neurons that were seeded on 45 and 125 µm diameter beads were fixed at DIV 4 and stained for smi-312, an axonal marker, to demonstrate that neuron maturation occurs at the same rate for all bead sizes. Immuno-staining revealed that the neurons were polarized on both the smaller and larger beads, independently of the number of cells per bead (FIG. 1, Panels d-i). For all cultures, the total area covered by the beads was kept fixed, and the number of seeded cells was kept constant. Under these conditions, the 45 µm diameter beads carried at least one neuron when the number of cells was equal to the number of beads (see Supplementary Material), whereas for the same number of cells seeded, the 125 µm diameter beads carried 10 times more cells, as illustrated in FIG. 1, Panels d-i.

Example 4

Tuning the Properties of the 3D Networks

The diameter of the beads and the density of cells in solution during plating were both adjusted in order to control the properties of the 3D networks. Based on the geometry of the assembly depicted in FIG. 3, Panel a, the number of cells per unit volume was estimated in relation to both bead diameter and the number of cells per bead (FIG. 3, Panel d). For a given volume, a hexagonal compact assembly of 45 µm diameter beads was estimated to be composed of 19 times more beads than an assembly made from 125 µm diameter beads. Under the seeding conditions used (see Methods), a surface density of 75 k cells/cm$^2$ corresponded to an average of 5 neurons per 45 µm diameter bead and about 35 neurons per 125 µm diameter bead. Therefore the cell density per mm$^3$ in the final assembly was about 2.7 times higher for the 45 µm diameter beads (FIG. 3, Panel e). Hence, the most effective way to increase cell density, while allowing for a low number of cells per bead, was to use smaller beads (FIG. 3, Panel e). The upper limit to cell density was set by the free volume left by the beads and was defined by bead packing order, representing 32% of the total volume for the hexagonal compact assembly. In practical terms, densities of up to 75 k cells/mm$^3$ were achieved with 45 µm diameter beads, i.e. close to the 91 k cells/mm$^3$ measured in mouse brain cortex (27).

The pattern of connectivity between neurons on beads within the 3D hexagonal array was spatially constrained by the 12 contacts made between each bead and its neighbors: 6 within the plane, and an additional 3 in the plane above and 3 in the plane below (FIG. 3, Panel a), yielding 12 equidistant connection points. For hexagonal ordered assemblies, the density of connection points depended inversely on the bead radius cubed, while the distance between contact points was linearly related to the bead radius. Thus, the neuronal connectivity of the networks that formed on these bead arrays followed bead size, with smaller beads leading to assemblies with higher connectivity.

Example 5

Guiding Inter-Layer Axo-Dendritic Connectivity Via Directed Growth

Process extension from one population of neurons to another was directed by inserting guiding beads into the assembly. Guiding beads were first coated with the attractant signaling molecule cAMP, which guides axonal growth (28). The cAMP-coated beads, which bore no cells of their own, were assembled into a single-layer packed array on top of a 2D culture of neurons growing on a cover slip (see schematic representation in FIG. 4, Panel a). Axons from the neurons on the cover slip that encountered a cAMP-coated bead adhered to the bead and grew upward, extending over the surface of the cAMP-coated bead. The axons grew at a rate of ~50 μm/day. This rate of growth was independent of bead size. Since the distance between bead contacts was proportional to bead radius, axons bridged to neighboring beads more quickly in cultures containing smaller beads. Within three days, the axons went on to explore the connection points between a bead and as many as three of its neighbors in the 45 μm bead arrays (FIG. 4, Panel a, arrow).

The axon guidance effect of cAMP was strongest in the first two days following deposition of the cAMP-coated bead layer. Staining for the neurite marker Tuj-1, which stains both axons and dendrites, and smi-312, which stains only axons, revealed that axons grew upward from the neurons on the cover slip and onto the beads. Axons (blue) were readily distinguished on the cover slip (layer 1) among all of the neuritis (red) (FIG. 4, Panels b-d). In the first two days after layering on the cAMP-coated beads, the only processes that grew onto the beads from the neurons on the cover slip were axons (FIG. 4, Panel a) and (FIG. 4, Panels e-g). However, after seven days in culture, the cAMP guidance effect wore off, and dendrites from the neurons on the cover slip (layer 1) also appeared on the layer-2 beads (FIG. 4, Panels h-j).

Figure 4:
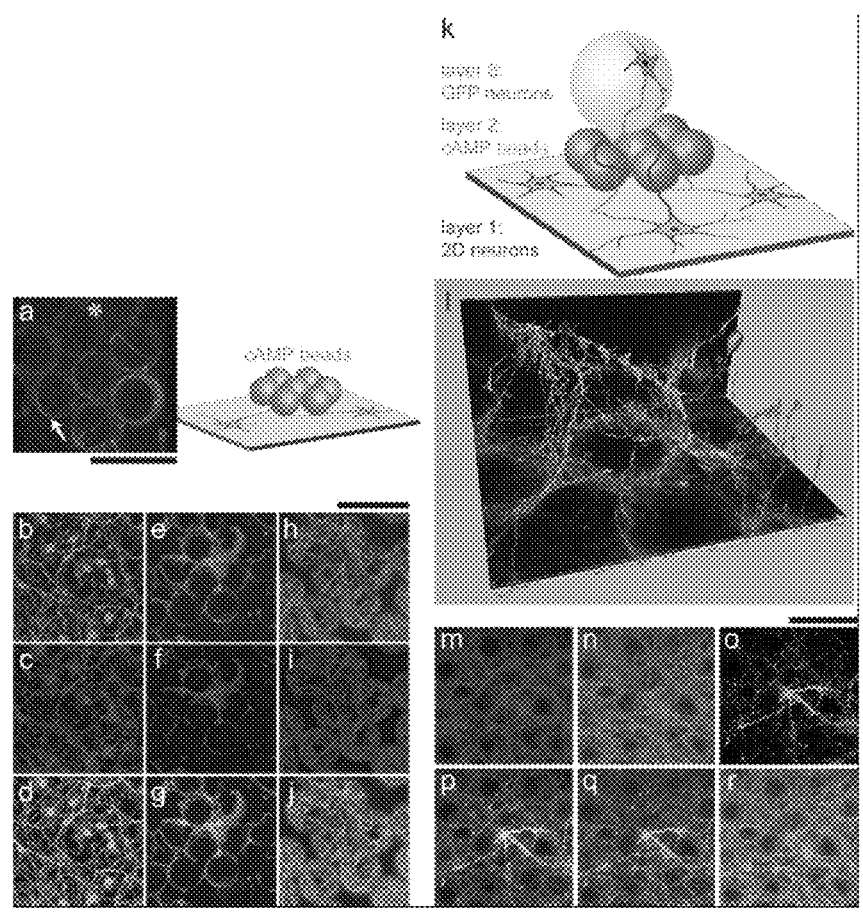
FIG. 4, Panels a-j show that a layer of guidance beads directs polarized process growth.

Another bead layer was then added (layer 3), which consisted of beads coated with neurons expressing GFP (see schematic representation in FIG. 4, Panel k). This was done after 5 days of culture, when the cAMP-coated beads in layer 2 had lost the ability to attract axons. As a result, layer-3 GFP-positive dendrites extended onto the intermediate layer 2, where they encountered the axons from layer 1. This was observed from reconstruction of confocal z-series frames using filament tracing software (FIG. 4, Panel 1). GFP processes from cells in layer 3 that reached layer 1 were only stained by Tuj-1 (FIG. 4, Panels m-r), indicating that only the dendrites of layer-3 cells reached the bottom layer. An axonal stain with smi-312 showed that axons from the bottom layer climbed up into the guidance layer (layer 2) to reach the upper (layer 3) GFP neurons (FIG. 4, Panel 1). Thus, an intermediate layer of cAMP-coated beads can be used to mediate directional connections between neurons growing in layers above and below.

Example 6

Formation of Functional Synaptic Connections within the 3D Networks

The contacts created between cells from layers 1 and 3, as described above in Example 3, were tested for functional synaptic activity using a light-gated glutamate receptor (LiGluR6) containing an attachment site for the photo-switched tethered glutamate molecule MAG-1(22-24). LiGluR6 was transfected exclusively into the neurons on the over slip several days before the addition of the guiding bead layer. The cAMP-coated bead layer was then added, as described above in Example 3, followed by addition of a third bead layer containing GFP-expressing neurons. At DIV-12 the neurons were labeled with the tethered photoswitch MAG-1 and rhod-2, a calcium-sensitive fluorescent indicator. MAG-1 selectively confers optical excitation only onto neurons expressing LiGluR6(24). The rhod-2 dye infiltrated both the neurons on the cover slip and those on the upper layer of beads, enabling use of confocal Ca++ imaging to monitor neuronal activity in both cell layers. This cell layout (FIG. 5, Panel a, schematic) was designed to selectively stimulate the cover slip neurons with light, while monitoring activity in both layers: layer 1 with LiGluR6 neurons and upper layer 3 with neurons that did not express LiGluR6, but were marked with GFP.

Figure 5:
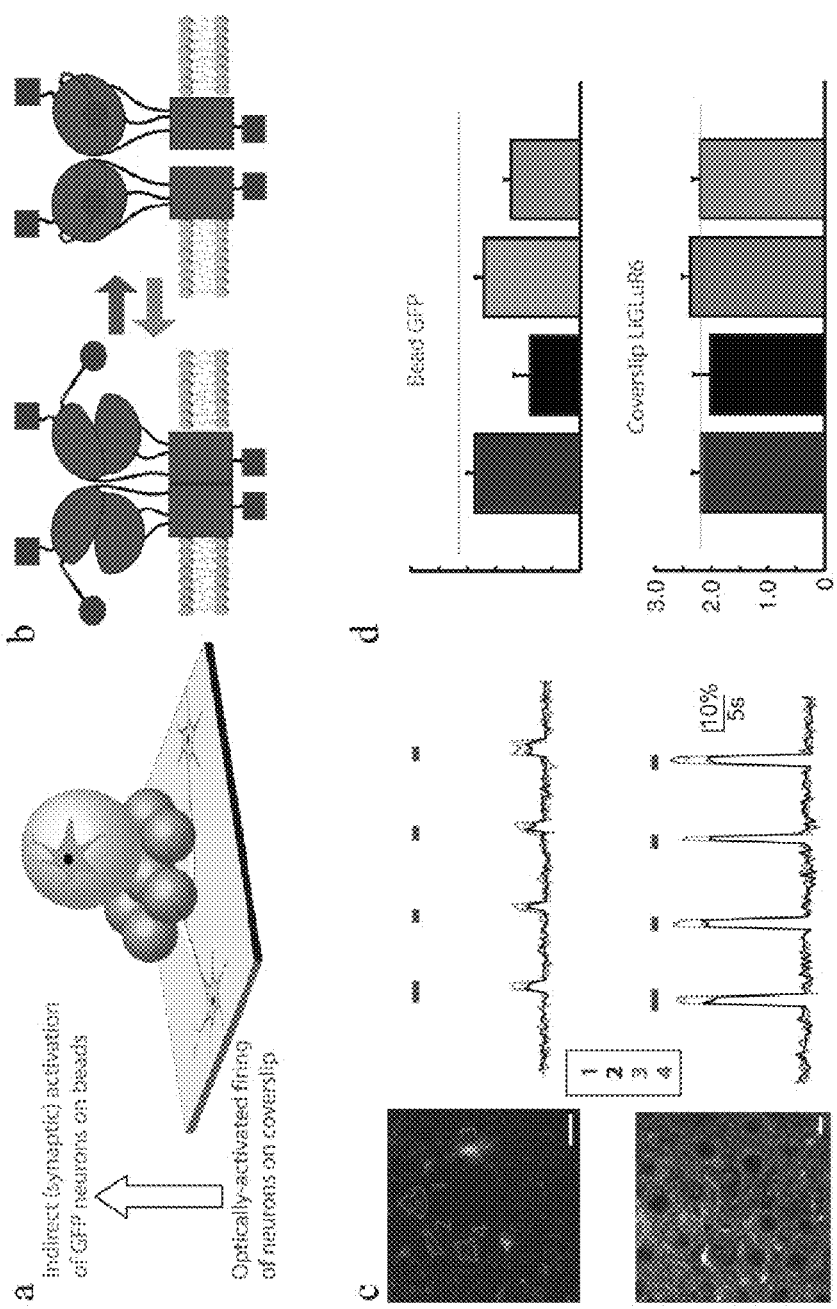
FIG. 5, Panel a is a schematic of the directed 3D neuronal assembly. Neurons cultured on a cover slip (lower blue layer) were transfected with LiGluR6. One week later, the layer of cAMP-coated beads was added as a guidance layer (layer 2, orange balls). Following 2 days of growth of axons from the cover slip into the layer-2 beads, a third layer of beads carrying neurons that were separately transfected with GFP was added. These GFP neurons extend dendrites down into layer 2 and meet the axons of layer 1.

Illumination at 390 nm (using a frequency doubled 780 nm pulsed laser) was used to activate LiGluR6 and illumination at 543 nm was used to turn the activity off (FIG. 5, Panel b, schematic). The shorter wavelength reliably and repeatedly triggered an influx of Ca++ into the LiGluR6-expressing neurons on the cover slip, while the longer visible wavelength turned this activity off and resulted in a return to resting Ca++ levels, as shown by the confocal time series (FIG. 5, Panel c, bottom). Ca++ imaging of the GFP layer of neurons on the beads revealed that they too were activated by illumination at 390 nm and deactivated at 542 nm (FIG. 5, Panel c, top), even though they did not express LiGluR6. Neurons that did not express LiGluR6, but which were labeled with MAG-1, were not activated by illumination at 390 nm (28). Thus, the Ca++ responses observed in GFP-expressing neurons indicated that the connections between the axons of the LiGluR6-expressing neurons on the cover slip and the dendrites of the GFP-expressing neurons on the beads contained functional synapses, with the neurons on the cover slip being pre-synaptic.

Neurons on the cover slip responded reliably and similarly to optical stimulation, whereas the GFP-expressing cells on the beads sometimes responded similarly (FIG. 5, Panel c) and other times showed responses that differed in strength from neuron to neuron, even on the same bead (FIG. 5, Panel d). These results demonstrated the possibility of using the all-optical approach of light-gated ion channels and activity indicators to assess the spatial and temporal properties of synaptic transmission in the 3D neuronal arrays.

Example 7

Physical Manipulation of Neuron Contacts

The 45 and 125 μm diameter beads were small enough that they could be suspended in solution and taken up with a pipet, and yet dense enough that they could settle to the bottom of a dish and remain insensitive to small disturbances in fluid flow (Pautot et al., 2008). This property enabled differentiated neurons growing on beads to be placed directly onto conventional 2D neuronal cultures growing on cover slips. The beads could then be rolled to desired locations, and thus specific targets for connectivity could be defined. FIG. 1, Panel j illustrates the basic approach: two neurons—one cultured on a bead, the other on the cover slip, which differed in gene expression pattern because they had been separately transfected, and brought into contact in a controlled fashion. The bead-supported neurons expressed a cytosolic green fluorescent protein (GFP) and the neurons grown on the cover slips expressed a fusion protein of neurexin, a presynaptic integral membrane protein that mediates adhesion at synapses, and a cytosolic red fluorescent protein (RFP). Two days after infection with virus that delivered the GFP gene, the beads were dropped on the 2D neuronal cultures and positioned with a micropipet. FIG. 1, Panel k shows a total internal reflection fluorescence microscopy image of the successful contact point between the genetically different neurons.

Example 8

Synapse Formation in 2D Arrays of Neurons

Beads coated with neurons were allowed to assemble into close-packed 2D arrays. The arrays were then fixed and stained with alpha-tubulin antibody, which highlights neuronal processes, and synapsin antibody, which identifies presynaptic terminals. The resulting images showed dense axonal and dendritic processes crossing between beads (FIG. 1, Panel 1; arrows). The density of synapses was similar to what was found on 2D cover slip cultures at similar cell densities. Hence, neurons that are confined to a bead for manipulation purposes can bridge to surrounding surfaces to form synapses with neighboring cells once they have been positioned, and can form functional 2D arrays with similar synaptic density to 2D cover slip cultures of neurons.

Example 9

Transplantation of Neurons Attached to Beads

Figure 6:
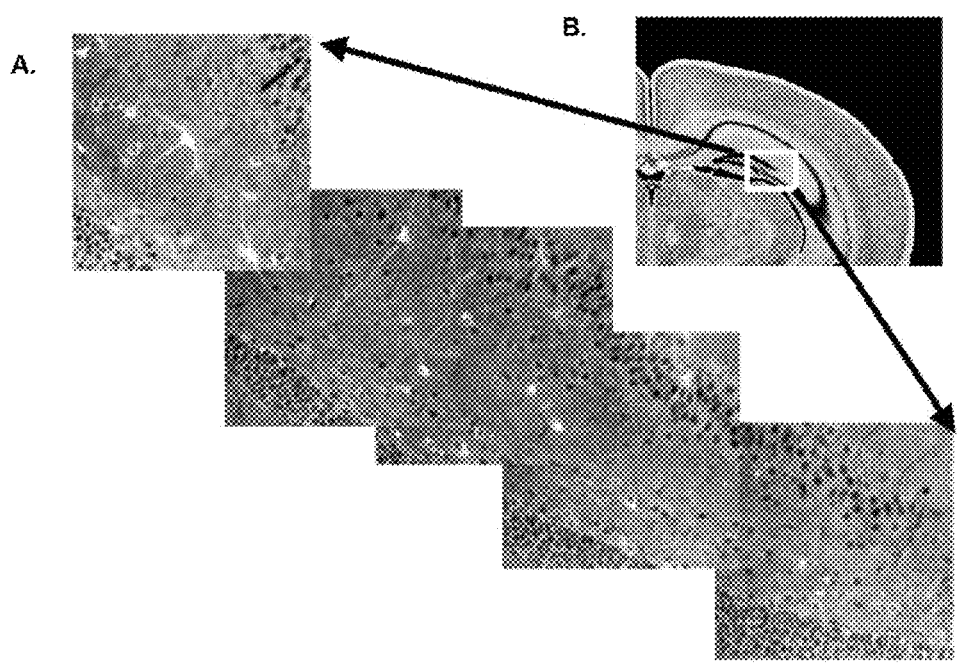
FIG. 6 shows transplanted neurons in the adult rat hippocampus.
Figure 7:
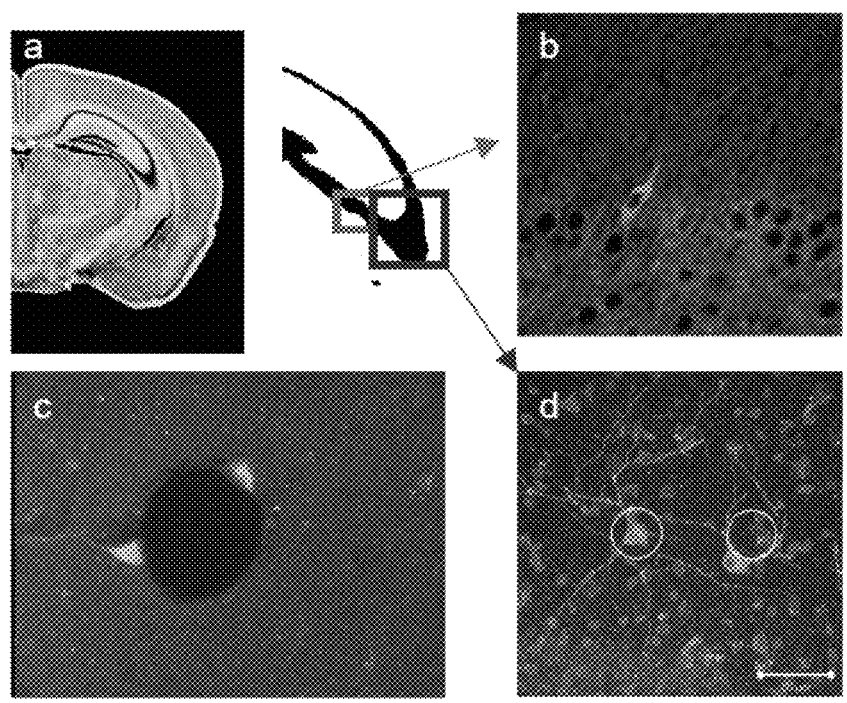
FIG. 7 shows in vivo neuron transplantation. Postnatal day 1 rat hippocampal neurons, transfected with GFP on DIV 3 and injected into right hippocampus of 6 weeks old rats. One week later, the animal was sacrificed and brain slices were fixed and stained with GFP antibody (white) and with Nissl (black) nuclear marker.

Neurons growing on 45 μm beads were transfected to express GFP under a synapsin promoter. On DIV 4-5, the GFP-neuron-bearing beads were injected stereotactically into the right CA3 region of the hippocampi of 6 weeks old rats (ref.+method). One week after injection of the beads, the animals were sacrificed, and 100 μm-thick brain slices were imaged to determine the status of the injection site. FIG. 6 shows a representative example. GFP-positive neurons were found between the dente gyms (DG) and the CA3 region in an area of ~600 μm diameter around the injection site. Bead transplantation was performed in 6 animals (3 separate surgeries with 3 separate neuron-bead cultures). In all of the animals, the GFP positive cells sent processes off of the beads and into the host tissue (FIG. 7, Panels c-d), and 6 to 28 GFP neurons per slice were observed around the injection point. The highest density of GFP-positive processes was consistently found in CA3 (FIG. 7, Panel a), suggesting that this region is more receptive to transplant integration. In contrast, in animals that were injected with neurons that were dissociated from the beads, GFP positive cells could barely be distinguished (FIG. 7, Panel b), suggesting that these cells either did not survive the injection or did not grow well. Thus, bead supports facilitate the successful integration of differentiated neurons into an existing in-vivo network.

Example 10

Functional Integration of Transplanted Neurons

To assess if transplanted neurons make functional connections with the host neurons, neurons expressing both GFP and LiGluR6, which contains an introduced cysteine at position 439 that serves as an attachment site for the photo-switched tethered glutamate molecule MAG-1(22-24), were transplanted as described above in Example 9. One week after injection of the GFP/LiGluR6 neuron beads, animals were sacrificed, and 210 μm-thick hippocampal slices were prepared (method). The slices were incubated in artificial cerebrospinal fluid (ACSF) and labeled first with MAG-1 and then with rhod-2, a fluorescent calcium indicator. MAG-1 selectively confers optical excitation only onto neurons expressing LiGluR6 (24), whereas rhod-2 infiltrated all of the cells in the slice, enabling us to use confocal Ca++ imaging to monitor neuronal activity throughout the host neurons in the section, as well as in the bead-borne transplanted neurons.

Figure 8:
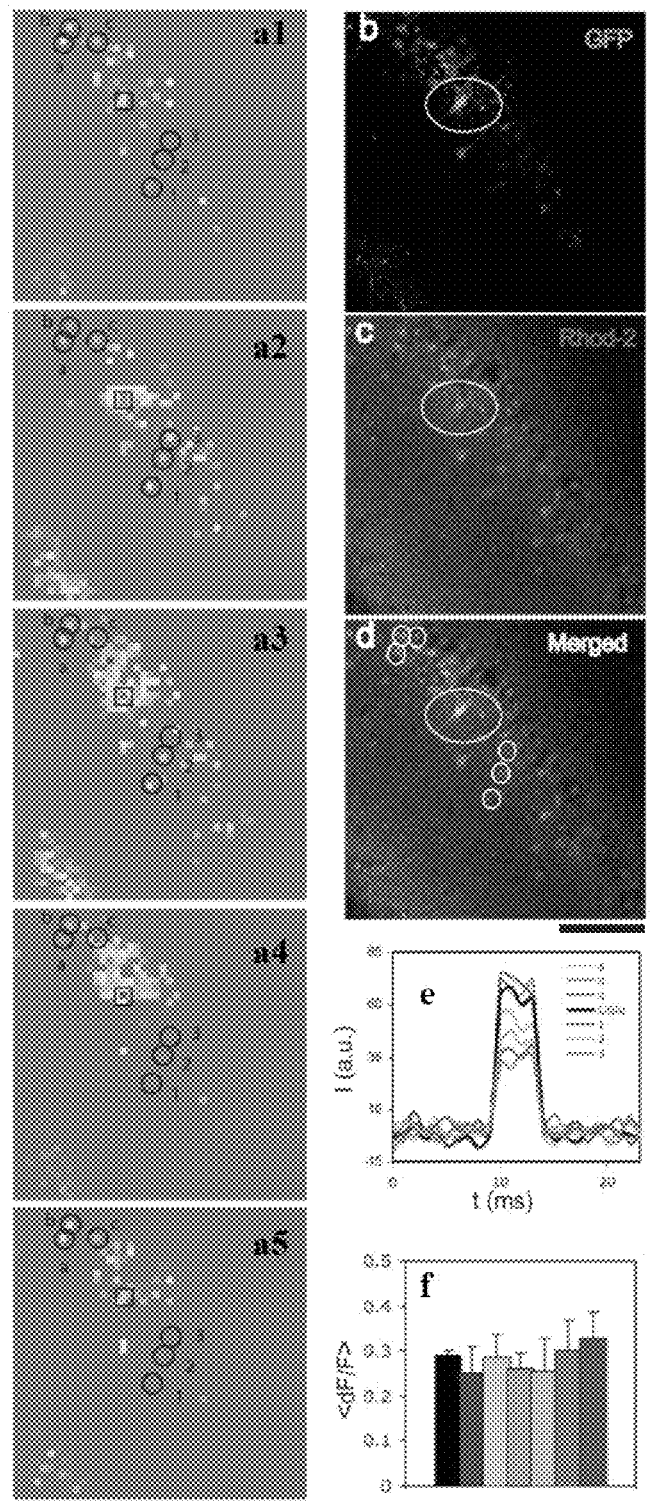
FIG. 8, Panel b shows live confocal imaging of calcium response in a hippocampal slice containing a transplanted LiGluR6 neuron expressing GFP, and FIG. 8, Panel c shows labeling with a calcium indicator, Rhod-2.

Illumination at 390 nm (using a frequency doubled 780 nm pulsed laser) was used to activate LiGluR6 and illumination at 543 nm was used to turn the activity off. The illumination at 390 nm reliably triggered a rise in Ca++ in the GFP/LiGluR6 transplanted neurons in the DG region (FIG. 8, Panels a-c), and the illumination at 543 nm turned this activity off and resulted in a return to resting Ca++ levels (FIG. 8, Panel e, black line). Ca++ imaging of the surrounding GFP-negative host neurons revealed that they too were activated by illumination at 390 nm and deactivated at 543 nm (FIG. 8, Panel e, colored lines), even though they did not express LiGluR6. It should be noted that isolated neurons that do not express LiGluR6, but which are labeled with MAG-1, are not activated by illumination at 390 nm (24). Thus, the Ca++ responses observed in the GFP-negative host neurons around the transplanted GFP/LiGluR-positive neurons indicate that the axons of the transplanted LiGluR6-expressing neurons make functional synapses with the dendrites of the host DG and CA3 neurons. ΔF/F was calculated for 6 neurons distributed around a single transplanted neuron for a train of seven UV stimulations (FIG. 8, Panel f). Whereas the ΔF/F of the directly stimulated transplanted LiGluR6 neuron had little variability from pulse to pulse, the host neurons were more variable from neuron to neuron and from pulse to pulse, consistent with their activation being mediated via synaptic connections and with those connections having some heterogeneity across the slice. Host neurons that were farther from the transplanted neuron did not respond to the light pulses, suggesting that the transplanted neurons have a limited reach and can only produce strong enough synaptic excitation of nearby neurons to produce detectable rises in Ca++. These results indicate that within one week following transplantation, the bead-borne neurons become functionally integrated into the network of the host brain.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method for forming a three dimensional culture of neuronal cells, said method comprising:
 depositing a first population of microparticles on a solid substrate, wherein said depositing forms a single first two-dimensional layer of said microparticles, wherein the solid substrate comprises a layer of neuronal cells and wherein said first population of microparticles is coated with cAMP that attracts axons of the neuronal cells;
 culturing the neuronal cells for a period of time sufficient for growth of the axons of the neuronal cells to the first population of microparticles; and
 depositing a second population of microparticles comprising neuronal cells on the surface of said first two-dimensional layer, wherein said depositing forms a single second two-dimensional layer of said microparticles, thereby forming the three dimensional culture of the neuronal cells.

2. The method of claim 1, wherein said neuronal cells are assayed for neuronal activity.

3. The method of claim 2, wherein said assaying for neuronal activity comprises staining the neuronal cells with an antibody that binds to a neuronal cell process.

4. The method of claim 3, wherein said neuronal cell process is a dendrite or an axon.

5. The method of claim 1, wherein said neuronal cells are transfected with a gene of interest encoding a detectable molecule; and
wherein said neuronal cells are assayed for neuronal activity by detecting said detectable molecule, wherein the detectable molecule is a fluorescent protein and wherein the neuronal activity comprises growth of a neuronal cell process or synaptic activity.

6. The method of claim 5, wherein said neuronal activity comprises growth of a neuronal cell process.

7. The method of claim 6, wherein said neuronal cell process is a dendrite or an axon.

8. The method of claim 5, wherein said fluorescent protein is Green Fluorescent Protein or Tandem-Dimer-Tomato.

9. The method of claim 5, wherein said fluorescent protein is under the control of a synapsin promoter.

10. The method of claim 5, wherein said detectable molecule is a light-gated glutamate receptor.

11. The method of claim 1, wherein said neuronal cells are cultured in a medium that contains a mitotic inhibitor.

12. The method of claim 11, wherein said mitotic inhibitor is araC.

13. The method of claim 1, wherein said microparticles are silica beads, latex beads, agarose beads, collage beads, Polyacrylamide beads, PLL-coated beads or PLGA beads.

14. The method of claim 1, wherein said compound that provides for attachment of neuronal cells is poly-L-lysine.

* * * * *

UNITED STATES PATENT AND TRADEMARK OFFICE
CERTIFICATE OF CORRECTION

| | | |
|---|---|---|
| PATENT NO. | : 9,080,148 B2 | Page 1 of 1 |
| APPLICATION NO. | : 12/830999 | |
| DATED | : July 14, 2015 | |
| INVENTOR(S) | : Ehud Y. Isacoff | |

It is certified that error appears in the above-identified patent and that said Letters Patent is hereby corrected as shown below:

Specification

Please replace the existing GOVERNMENT RIGHTS statement in column 1, lines 10-15 of the patent, with the following:

--STATEMENT REGARDING FEDERALLY SPONSORED RESEARCH

This invention was made with government support under contract numbers NS050833 and EY018241 awarded by the National Institutes of Health. The government has certain rights in the invention.--

Signed and Sealed this
Second Day of February, 2016

Michelle K. Lee
*Director of the United States Patent and Trademark Office*